(12) United States Patent
Griego et al.

(10) Patent No.: US 8,277,395 B2
(45) Date of Patent: Oct. 2, 2012

(54) LUMEN MEASUREMENT DEVICES AND RELATED METHODS

(75) Inventors: John A. Griego, Blackstone, MA (US); Luis J. Maseda, Natick, MA (US); David E. Yamartino, Riverside, RI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1338 days.

(21) Appl. No.: 10/946,287

(22) Filed: Sep. 22, 2004

(65) Prior Publication Data

US 2006/0064039 A1    Mar. 23, 2006

(51) Int. Cl.
*A61B 5/103* (2006.01)
*A61B 5/117* (2006.01)
(52) U.S. Cl. ...................................................... 600/587
(58) Field of Classification Search .................. 600/300, 600/304, 551, 560, 561, 587, 593; 606/191, 606/192, 193, 194, 195, 196, 197, 198; 73/1.79, 73/1.81
See application file for complete search history.

(56) References Cited

U.S. PATENT DOCUMENTS

| | | | | |
|---|---|---|---|---|
| 4,566,465 A | * | 1/1986 | Arhan et al. | 600/591 |
| 5,010,892 A | * | 4/1991 | Colvin et al. | 600/587 |
| 6,039,701 A | * | 3/2000 | Sliwa et al. | 600/588 |
| 6,110,200 A | * | 8/2000 | Hinnenkamp | 623/2.11 |
| 2001/0039388 A1 | * | 11/2001 | Korotko et al. | 600/587 |
| 2005/0010138 A1 | * | 1/2005 | Mangiardi et al. | 600/587 |
| 2005/0131390 A1 | * | 6/2005 | Heinrich et al. | 606/1 |

* cited by examiner

*Primary Examiner* — Jeffrey G Hoekstra
(74) *Attorney, Agent, or Firm* — Finnegan, Henderson, Farabow, Garrett & Dunner, L.L.P.

(57) ABSTRACT

Various embodiments of a measurement device used to measure a size of a lumen and related methods of use are disclosed. For example, the device may include a proximal handle, a distal member including a radially expandable portion, a control member connecting the proximal handle to the distal member, and a measurement indication member for displaying a value indicative of a size of the expandable portion. The radially expandable portion may be configured to expand from a contracted state to an expanded state to measure the size of a lumen.

37 Claims, 8 Drawing Sheets

LUMEN MEASUREMENT DEVICES AND RELATED METHODS

DESCRIPTION OF THE INVENTION

1. Field of the Invention

This invention relates to measurement devices and related methods thereof. In a particular embodiment, this invention relates to medical measurement devices and methods for measuring, for example, a patient's body lumen.

2. Description of the Related Art

In various medical procedures, it is desirable to know a measurement, for example the diameter, of a body lumen or cavity. Such lumens or cavities include lumens of the gastrointestinal tract, urological tract, pulmonary tract, circulatory system (such as veins or arteries, for example), and body organs, for example. As an example, prior to or during an endoscopic procedure, a physician may require knowledge of a patient's lumen or cavity size in selecting medical devices suitable for use in that particular lumen. In particular, when the procedure involves placement of a stent in a patient's body lumen, such as, for example, a tracheal, bronchial, or esophageal lumen, an ill-sized stent may not fully deploy and/or cause excessive granulation or migration. Therefore, accurate determination of the lumen size may enable the physician to confidently select the suitably sized stent and associated medical devices, so as to eliminate or reduce the above-mentioned undesirable effects and to enhance the effectiveness of the medical treatment.

SUMMARY OF THE INVENTION

Therefore, an embodiment of the invention relates to a measurement device that can accurately measure a lumen or cavity size and directly translate the measured value in a visual indicating member. While the present invention will be described in connection with a diameter measurement device, the invention may be applied to numerous other devices, such as catheters, that may require measurement of a portion extending radially or axially from the device. Examples of such devices may include any various therapeutic or diagnostic endoscopic laparoscopic, or other medical devices, including fluid injection catheters, snare catheters, and biopsy forceps, and other devices utilizing an expansion mechanism, such as, for example, stent placement/deployment catheters, dilatation catheters, or occlusion catheters.

To attain the advantages and in accordance with the purpose of the invention, as embodied and broadly described herein, one aspect of the invention may provide a device comprising a proximal handle, a distal member including a radially expandable portion, a control member connecting the proximal handle to the distal member, and a measurement indication member for displaying a value indicative of a size of the expandable portion. The expandable portion may be configured to expand from a contracted state to an expanded state to measure the size of a lumen, and actuation of the proximal handle may cause the expandable portion to expand.

The indication member may be located proximate the distal member. In another aspect of the invention, the indication member may be located proximate the proximal handle. In still another aspect, the indication member may be integrally formed with the handle.

According to another aspect of the invention, the indication member may include a rotatable member configured to rotate in relation to expansion and contraction of the expandable portion. The rotatable member may include a plurality of measurement marks for displaying the size of the expandable portion.

In still another aspect of the invention, the rotatable member may be configured to interact with the control member to rotate in relation to expansion and contraction of the expandable portion. In yet still another aspect, the rotatable member and the control member may be configured to translate axial movement of the control member into rotational movement of the rotatable member.

In another aspect of the invention, the value displayed on the measurement indication member may include at least one of diameter, radius, circumference, and cross-sectional area of the expandable portion. In still another aspect, the value displayed on the measurement indication member includes a type of other device suitable for use in the lumen.

In another aspect of the invention, the expandable portion may include at least one expandable member having a proximal end and a distal end and configured to radially outwardly expand upon a relative movement of the proximal and distal ends towards each other. The at least one expandable member may include a plurality of wires. The plurality of wires may be intermeshed to form a radially expandable sleeve.

In still another aspect of the invention, the at least one expandable member may include a bending portion to allow the expandable member to bend in a predetermined direction upon the relative movement.

In another aspect, the at least one of the distal and proximal ends may be coupled to the control member to cause the relative movement between the distal and proximal ends.

In still yet another aspect of invention, the control member may include a plurality of control members and the at least one expandable member may include a plurality of expandable members. Each of the plurality of control members may be connected to a corresponding one of the plurality of expandable members.

In accordance with another aspect of the invention, the distal member may be an integral, single-piece member. In still another aspect, the at least one expandable member may include a plurality of expandable members symmetrically or asymmetrically arranged in a radial direction.

In still another aspect of the invention, the expandable portion may include at least two expandable members. One of the at least two expandable members may be configured to be decoupled from the other of the at least two expandable members. In an exemplary embodiment, one of the at least two expandable members may be configured to expand and/or contract relative to the other of the at least two expandable members.

Another aspect of the invention may provide a measurement device comprising a proximal handle, a distal member including an axially extendable portion configured to extend from a first position to a second position, a control member connecting the proximal handle to the distal member where actuation of the proximal handle may cause the extendable portion to extend, and a measurement indication member for displaying a value indicative of the axial extension or position of the extendable portion.

In still another aspect of the invention, the indication member may be located proximate the distal member or the proximal handle. In yet still another aspect, the indication member may include a rotatable member configured to rotate in relation to extension and retraction of the extendable portion. The rotatable member may include a plurality of measurement marks for displaying the axial extension or position of the extendable portion.

In another aspect, the rotatable member may be configured to interact with the control member or the extendable portion to rotate in relation to extension and retraction of the extendable portion. The rotatable member may be configured to translate axial movement of the control member or extendable portion into rotational movement of the rotatable member.

According to another aspect of the invention, a method of measuring a size of a lumen may be provided. The method may include providing a device having a radially expandable portion configured to expand from a contracted state to an expanded state, positioning the expandable portion of the device within the lumen, expanding the expandable portion against an inside surface of the lumen, and displaying a measured value indicative of a size of the expandable portion. The method may include a step of contracting the expandable portion from the expanded state to the contracted state.

In still another aspect of the invention, the lumen may be a tracheal, bronchial, or esophageal lumen. In another aspect of the invention, the step of positioning the expandable portion of the device may include advancing the device through an endoscope.

In yet still another aspect of the invention, the step of displaying a measured value may include displaying at least one of diameter, radius, circumference, perimeter, and cross-sectional area of the expandable portion, or a type of other devices suitable for use in the lumen.

Another aspect of the invention may further include a step of converting a measured dimension of the lumen to the measured value that corresponds to a dimension of a normalized circular lumen. The measured value may be a diameter of the normalized circular lumen. In still another aspect of the invention, the step of converting may be performed mechanically or electronically. In yet still another aspect of the invention, the measured value may be displayed mechanically or electronically.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

In the drawings.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

Figure 1:
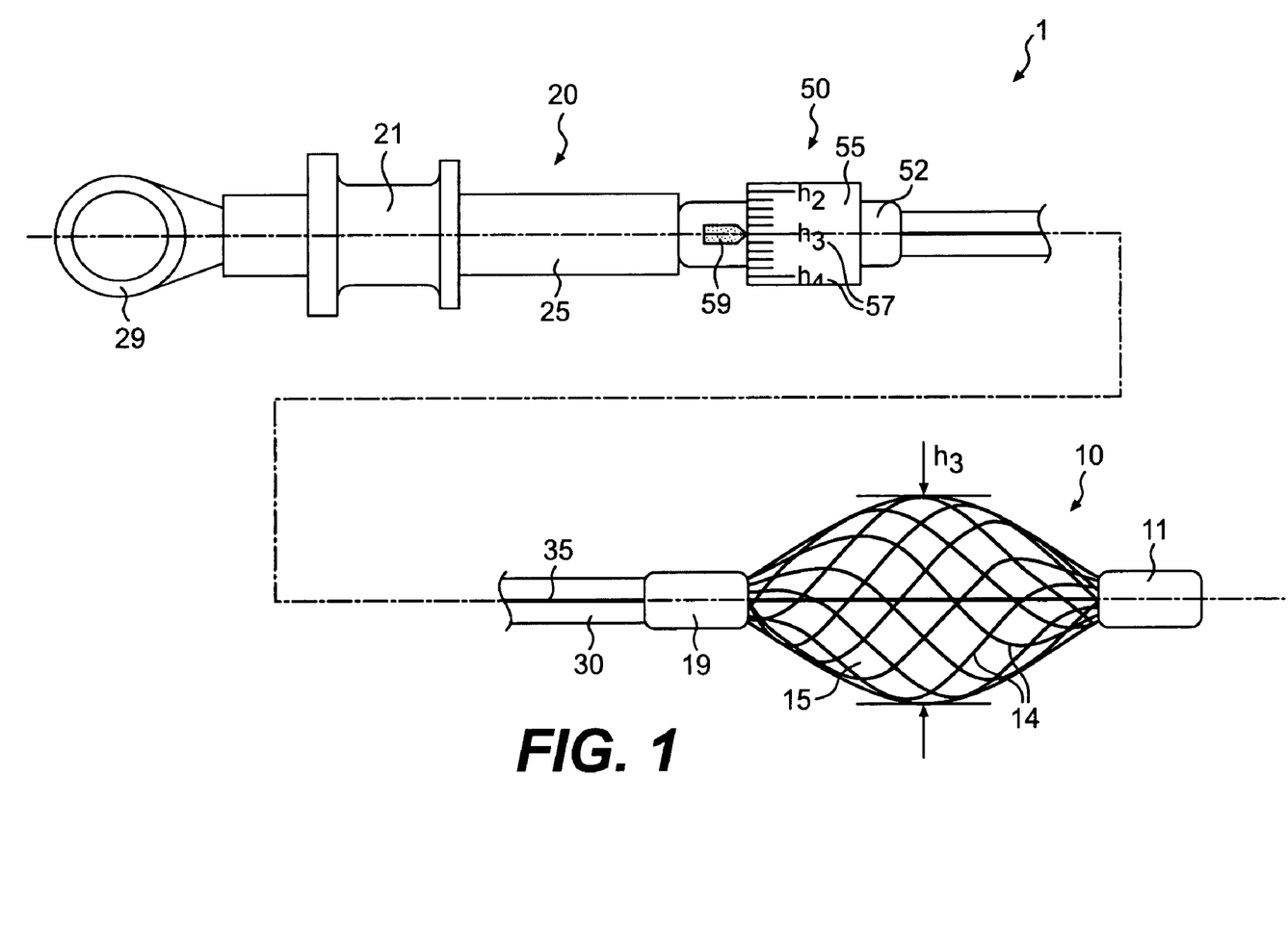
FIG. 1 is a schematic side view of a lumen measurement device, according to an exemplary embodiment of the invention, with its distal member in an expanded state.

According to an exemplary embodiment of the invention, FIG. 1 illustrates a lumen measurement device 1 having a capability for measuring a dimension (e.g., diameter, radius, circumference, cross-sectional area, etc.) of a lumen or cavity and translating the measured value to a visual indicator member. While the invention will be described in connection with a particular medical procedure, the invention may be applied to, or used in connection with, any other medical procedures, or numerous other non-medical applications that may require measurement of a hollow lumen or cavity. The invention may also be used in an application that may require an expansion mechanism, such as, for example, deployment of a stent or widening of a stricture. For example, the expansion mechanism may be used to restore a cross-sectional area of an impeded lumen by reciprocal and/or rotational scraping of the impeded lumen. Additionally or alternatively, the expansion mechanism may be used to control fluid flow in a hollow lumen or cavity. For example, the expansion mechanism may be used to prevent fluid from flowing in a particular direction by providing a temporary occlusion and/or redirection of flow. The expansion mechanism may also be used to provide a filter mechanism. Alternatively or additionally, the expansion mechanism may conduct electric current for use in, for example, electrocautery (e.g., 360° cautery) by connecting at least a portion of the expansion mechanism to a suitable current generator.

Figure 2:
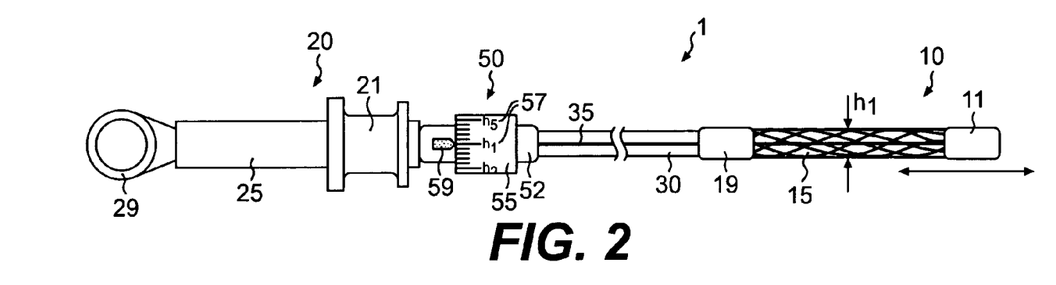
FIG. 2 is a schematic side view of the lumen measurement device shown in FIG. 1, with its distal member in a contracted state.

As shown in FIGS. 1 and 2, the lumen measurement device 1 may include an elongated tubular member 30, an expandable distal member 10 coupled to the distal end portion of the tubular member 30, a proximal handle assembly 20 coupled to a proximal end of the tubular member 30, and a measurement indicating member 50 used to indicate the measured lumen dimension to a user. The device 1 may also include a control member 35 that may extend from the handle assembly 20 to the distal member 10 to control the operation of the expandable distal member 10 from the handle assembly 20. In various exemplary embodiments, the device 1 may be used with a flexible guide member (not shown) for guiding insertion of the distal member 10 through a body lumen or cavity, and/or a suitable endoscope to view the insertion process or the operation of the expandable distal member 10.

The elongated tubular member 30 may be sufficiently flexible to traverse through a tortuous body cavity, yet stiff enough to prevent lumen collapse when tension on the control member 35 is generated. For example, the tubular member may be formed of a wire coil, preferably coated with a suitable biocompatible material, such as, for example, polytetrafluoroethylene (PTFE), polypropylene (PP), polyethylene (PE), Nylon, Pebax, Polyimide, or any other materials known in the art, on the outer surface of the wire coil. Alternatively, or in addition, the tubular member 30 may include a tubular sleeve member, made of a polymer material (e.g., Teflon, PTFE, Vectran liquid crystal polymer, or Kevlar®), a metallic material (stainless steel, nitinol, or platinum), and/or any other suitable material known in the art. In an exemplary embodiment, the tubular member 30 may form a braided tube made from polymer or metallic fibers. In another exemplary embodiment, the tubular member 30 may be formed of a combination of polymer and metallic fibers, so as to promote both flexibility and radiopacity.

In addition, the tubular member 30 may include a hydrophilic lubricious material or other suitable lubricating material to reduce friction. In another embodiment, at least a portion of the tubular member 30 may include barium sulfate or any other suitable material known in the art to promoting radiopacity.

The handle assembly 20 may include a thumb ring 29 fixedly attached to a main body 25, and a movable spool 21 slidably coupled to the main body 25, for manipulation of the expandable distal member 10. The proximal end of the tubular member 30 may be fixed to the distal end of the main body 25, while the proximal end of the control member 35 may be fixed to the movable spool 21 via a suitable connection mechanism known in the art. This handle configuration may permit the spool 21 to reciprocate along the main body 25 so as to effectuate axial movement of the control member 35 relative to the tubular member 30. As will be described herein, the reciprocal movement of the spool 21 may cause the expansion and contraction of the expandable member 15 of the distal member 10. The handle assembly 20 may also include a force limiting member (not shown), such as a spring or a locking member, so as to limit the actuation force applied to the handle during actuation.

The handle assembly 20 shown in FIGS. 1 and 2 with the slidable spool 21 is exemplary only. Other handle assemblies known in the art that can cause movement of the control member 35 may alternatively be used. For example, a handle assembly may include a scissors-like actuation mechanism for operating the control member 35.

The control member 35 may be flexible enough to pass through a tortuous body cavity, yet sufficiently stiff to resist minor compressive force, thereby permitting axial movement of the control member 35 relative to the tubular member 30. To aid this purpose, the control member 35 may optionally include an inner sleeve (not shown). The inner sleeve may also act as a bearing member between the control member 35 and the lumen of the tubular member 30. The sleeve may be formed of a polymer material, such as, for example, polytetrafluoroethylene (PTFE), Nylon, Pebax, polypropylene (PP), or polyethylene (PE). In an exemplary embodiment, the control member 35 may be made of stainless steel, nickel-titanium alloy, or a combination of the two, but any other suitable material known in the art may also be used. In another exemplary embodiment, at least a portion of the control member 35 or the sleeve may be coated with a lubricating material, such as, for example, liquid silicon, to facilitate the axial movement of the control member 35.

The control member 35 may form a hypotube capable of injecting fluid therethrough for use in a flushing or injection therapy. In addition, the control member 35 may be configured to conduct electrical current via an active cord connector (not shown) located in the handle assembly 20 to provide current to an end effector, such as, for example, a needle knife or biopsy forceps, or expandable member 15.

The expandable distal member 10 may include a distal end portion 11, a proximal end portion 19, and an expandable member 15 having its ends connected to the distal and proximal end portions 11, 19, respectively. The distal end portion 11 may be tapered so as to facilitate the insertion of the distal member 10 through a body lumen. One of the distal and proximal end portions 11, 19 may be fixedly connected to the distal end of the tubular member 30, and the other of the distal and proximal end portions 11, 19 may be connected to the control member 35, so as to cause a relative movement between the distal and proximal end portions 11, 19 upon axial movement of the control member 35 along the longitudinal axis of the device 1. For example, the proximal end portion 19 may be connected to the distal end of the tubular member 30, and the distal end portion 11 may be connected to the distal end of the control member 35, as shown in FIGS. 1 and 2. In various exemplary embodiments, the distal and proximal end portions 11, 19 may be connected to the tubular member 30 and/or the control member 35 via interference-fit, crimping, soldering, welding, fusing, adhesive, or any other suitable connection mechanism known in the art.

As best shown in FIG. 1, the expandable member 15 may include a radially expandable sleeve formed of a plurality of intermeshed metallic or polymer wires 14. The ends of each wire 14 may be connected to, or integrally formed with, the proximal or distal end portions 11, 19. In an alternative embodiment, the wires 14 may be directly connected to the distal end of the tubular member 30 or the control member 35. Alternatively, other suitable expandable members known in the art may be used.

In an exemplary embodiment, the wires 14 may be formed of a memory material such as, nickel-titanium alloy (i.e., nitinol), or other suitable material having sufficient elasticity.

The expandable member 15 may include a suitable lubricating material to reduce friction. The expandable member 15 may also include a suitable radiopaque material to promote radiopacity. In addition, the expandable member 15 may be configured to conduct electrical current supplied from an active cord connector located in the handle assembly 20.

In operation, an axial movement of the control member 35 may cause a relative movement between the distal and proximal end portions 11, 19, which may then cause the sleeve 15 to expand or contract. For example, as shown in FIG. 1, when the control member 35 is moved in the proximal direction by moving the spool 21 relative to the main body 25, the distal end portion 11, to which the control member 35 is connected, may be moved in the proximal direction, while the proximal end portion 19, connected to the distal end of the tubular member 30, remains in a stationary position, thereby causing a reduction in the distance between the distal and proximal end portions 11, 19. The reduction in the distance, in turn, may cause the expandable sleeve 15 to expand radially from its contracted state until the widest portion of the sleeve 15 contacts against a surface of a lumen being measured. The diameter of the expanded sleeve 15 may correspond to the diameter of the lumen at that location of the lumen. The measured diameter of the lumen may then be displayed on the indicator member 50, as will be described further in detail herein. To contract the sleeve 15 to its normal contracted state, the spool 21 may be slidably moved distally, causing the control member 35 to move distally and to cause the distal end portion 11 to move away from the proximal end portion 19, as shown in FIG. 2. With the distal member 10 in this contracted state, the device 1 may be withdrawn from the lumen or, if desired, moved to another location for taking another measurement.

Figures 3, 4, 5:
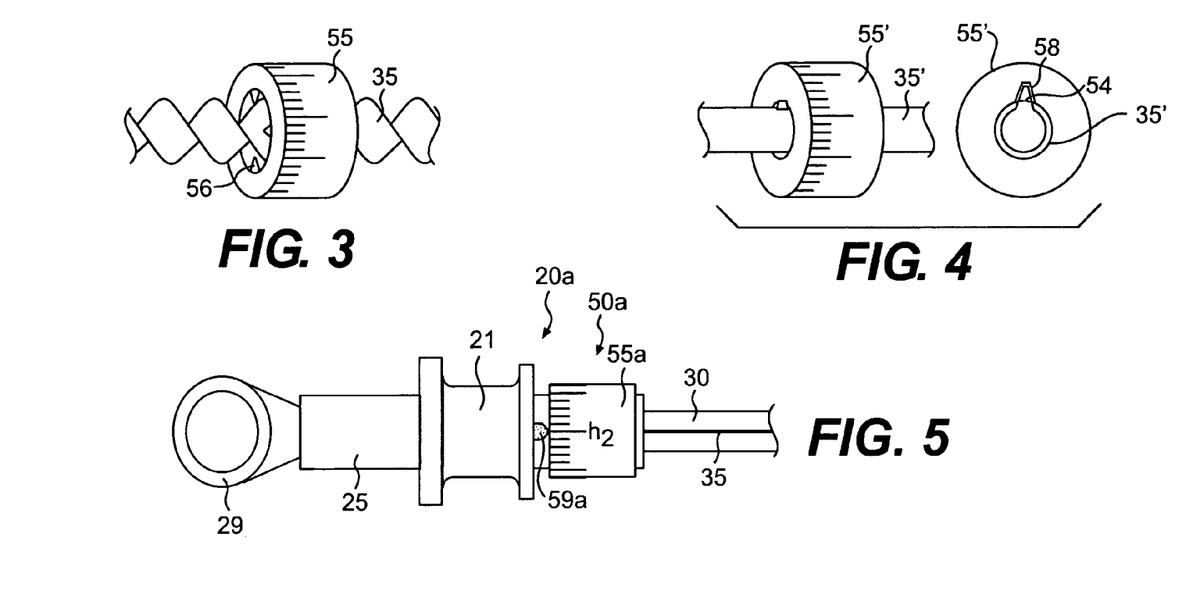
FIG. 3 is a schematic perspective view of a dimension indication member, according to an exemplary embodiment of the invention.
FIG. 4 is a schematic perspective view of a dimension indication member, according to another exemplary embodiment of the invention.
FIG. 5 is a partial schematic side view of a proximal portion of a lumen measurement device, according to another exemplary embodiment of the invention.
Figure 8:
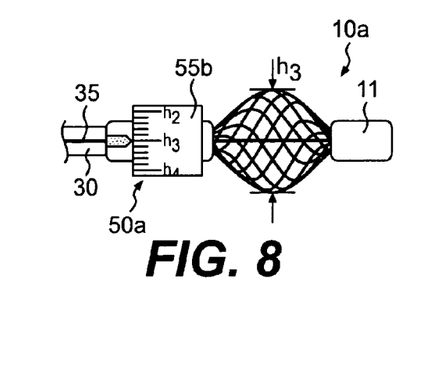
FIG. 8 is a partial schematic side view of a distal portion of a lumen measurement device, according to another exemplary embodiment of the invention.

The measurement indicating member 50 may include a main body 52 and a rotating member 55 rotatably coupled to the main body 52. In an alternative embodiment, the rotatable member 55 may not include a main body 52, and the rotatable member 55 may be directly coupled to the tubular member 30. In another alternative embodiment, the rotatable member 55a may be positioned on the proximal handle 20, as shown in FIG. 5, or on the distal or proximal end portion 11, 19 of the expandable distal member 10, as shown in FIG. 8.

As best shown in FIG. 1, the rotatable member 55 may include a measurement scale having a plurality of measurement marks 57 for displaying the measured value of the lumen size. In an exemplary embodiment, the measurement scale may have discrete measurement ranges or bands that may correlate the lumen size to a medical device size (e.g., stent size, balloon size, or shunt size). The indicating member 50 may also include a fixed alignment mark 59 on the main body 52 or on the tubular member 30 for designating which of the measurement marks 57 corresponds to the measured value of the lumen.

The operational aspect of the indicating member 50 will be described with reference to FIGS. 1-4. The indicating member 50 may include a hollow cylindrical member 55 configured to interact with the control member 35 to translate axial movement of the control member 35 to rotational movement of the cylindrical member 55. In an exemplary embodiment shown in FIG. 3, the cylindrical member 55 may include one or more projections 56 protruding from the inside surface of the cylindrical member 55 so as to form a rifled lumen. The control member 35 may have, on at least the portion associated with the cylindrical member 55, a spiral configuration, such that the cylindrical member 55 may rotate as the control member 35 moves axially. In another exemplary embodiment, one of the rotatable member 55' and the control member 35' may include a spiral groove 58, and the other of the rotatable member 55' and the control member 35' may include one or more protrusions 54 configured to associate with the spiral groove 58, as shown in FIG. 4. In this embodiment, as the control member 35' reciprocates axially, the protrusion 54 may ride along the spiral groove 58 so as to rotate the rotatable member 55'. Other suitable mechanisms known in the art for translating axial movement to rotational movement may alternatively be used.

The diameter of the expandable member 15 may be inversely proportional, either directly or indirectly, to the distance between the distal and proximal end portions 11, 19. According to the proportionality between the diameter of the expandable member 15 and the distance traveled by the control member 35, the rotatable member 55 may be marked with an appropriate measurement scale for displaying the diameter of the expandable member, which may represent the diameter of a lumen being measured. For example, as shown in FIG. 1, the measured value $h_3$ displayed on the rotatable member 55 represents the diameter $h_3$ of the expandable member 15, which is the diameter of the lumen being measured.

Figure 6:
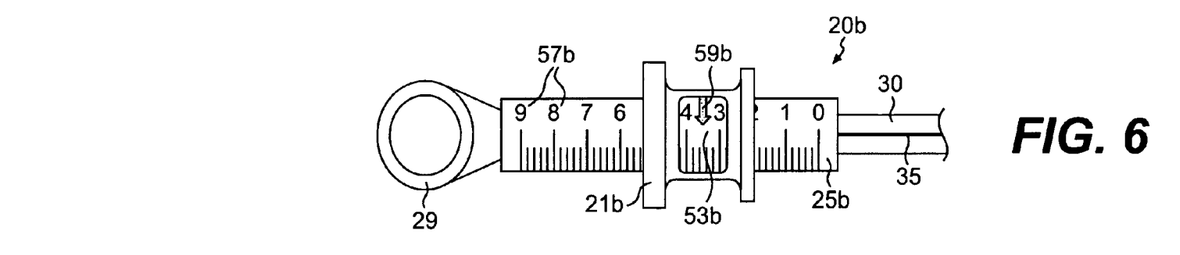
FIG. 6 is a partial schematic side view of a proximal portion of a lumen measurement device, according to still another exemplary embodiment of the invention.
Figure 7:
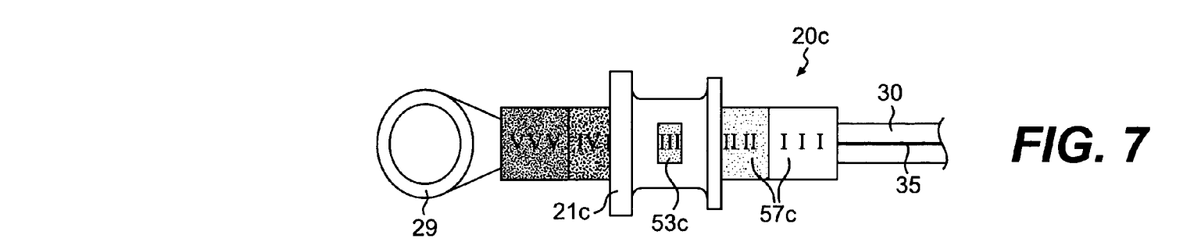
FIG. 7 is a partial schematic side view of a proximal portion of a lumen measurement device, according to still yet another exemplary embodiment of the invention.

According to another exemplary embodiment of the invention, a measurement indicating member 50 may not include a rotatable member 55 to display the measured value. Instead, as shown in FIGS. 6 and 7, an indicating member may be integrally formed with a handle assembly 20b, 20c. For example, the main body 25b of the handle assembly 20b may include a measurement scale having a plurality of measurement marks 57b, 57c for displaying the measured value of the lumen. In an exemplary embodiment, the measurement marks 57c may include discrete measurement values or measurement ranges that correlate the measured lumen size to a type of medical device suitable for that particular lumen size. For example, as shown in FIG. 7, each of the measurement marks 57c (e.g., I, II, . . . V) may represent a group of medical devices that have been classified by their sizes and determined to be suitable for use in a particular lumen size range. In an exemplary embodiment, type I devices may include medical devices suitable for use in a lumen having a diameter ranging between 0.5 and 2 unit length. The spool 21b, 21c may include an opening 53b, 53c, with or without a fixed alignment mark 59b, for indicating the measured value of the lumen being measured, as shown in FIGS. 6 and 7.

As mentioned above, the indicating member 50 may be located proximate the proximal handle 20, but may also be located anywhere along the tubular member 30. In an exemplary embodiment, the indicating member 50a may be positioned proximate the expandable distal member 10a, as shown in FIG. 8. In this embodiment, the indicating member 50a may be immediately adjacent the distal member 10a so that the indicating member 50a may be viewed together with the distal member 10a when the distal member 10a is visualized by a suitable imaging device, such as, for example, an endoscope, colonoscope, or sigmoidoscope.

Figure 9:
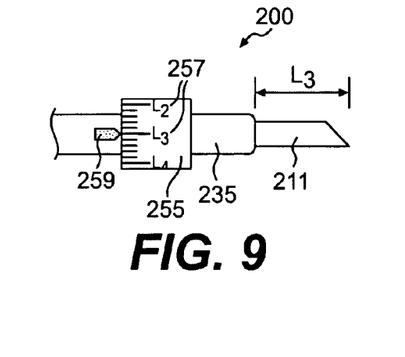
FIG. 9 is a partial schematic side view of a distal portion of another measurement device, according to still another exemplary embodiment of the invention.

In accordance with still another embodiment of the invention, the indicating member 50 may be used to measure the axial position or extension of, for example, a needle such as an injection needle or biopsy needle, as shown in FIG. 9, snare, biopsy forceps, or any other endoscopic or non-endoscopic medical device. In this embodiment, the rotating member 255 may interact with a needle 211 or a control member (not shown) that may control the axial movement of the needle 211, so that the axial position of the needle 211 or a length $L_3$ extended from a distal tip of a tubular member 235 can be measured and displayed on an indicating member 255. Any suitable operational mechanism, such as the embodiments described with reference to FIGS. 1-4, may be used to effectuate the axial movement. The indicating member 50 may also be used to measure a length or depth of a lumen or cavity.

FIGS. 10-16 illustrate an expandable distal member 110 of a lumen measurement device, according to another exemplary embodiment of the invention. The distal member 110 may be formed of a flexible material having sufficient elasticity and/or tensile strength. In various exemplary embodiments, the flexible material may include a polymer material, capable of being injection molded, so that at least a portion of the distal member 110 may be formed as a single piece. The one piece construction process may reduce the manufacturing costs and significantly enhance structural integrity of various parts. In another exemplary embodiment, at least a portion of the distal member 110 may be formed of a metallic material.

Figure 10:
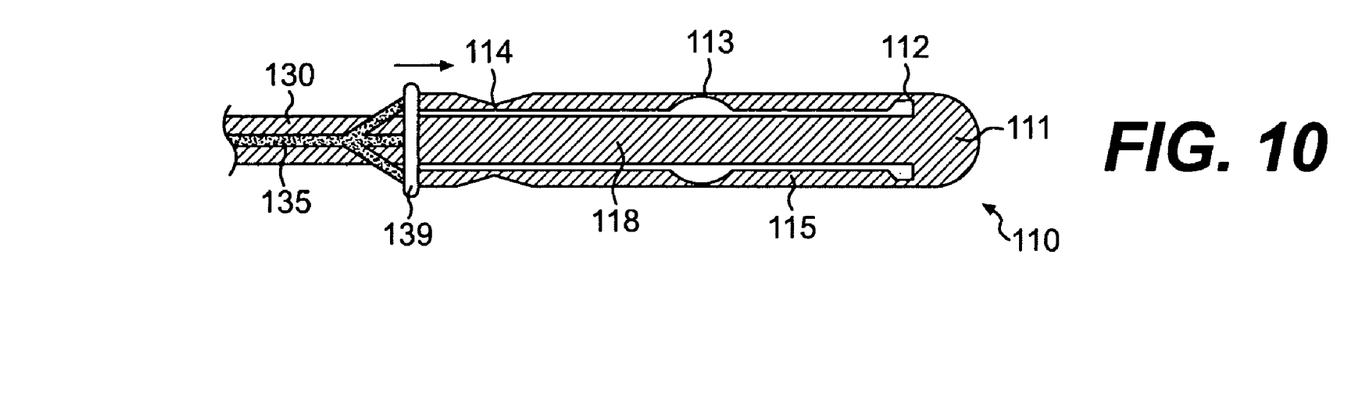
FIG. 10 is a partial schematic side view of a distal member, according to still yet another exemplary embodiment of the invention, illustrating the distal member in a contracted state.
Figure 11:
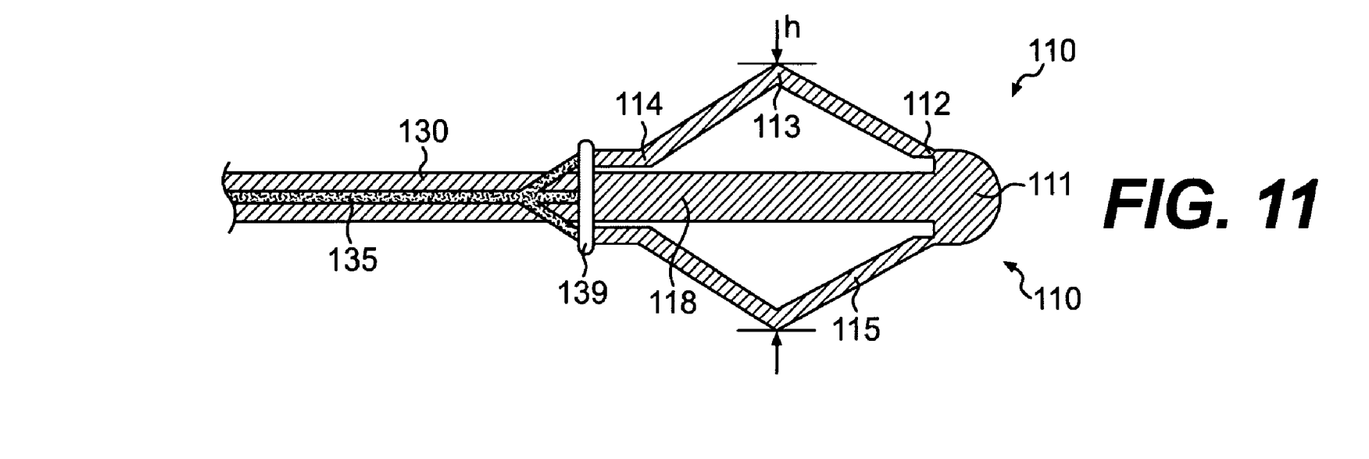
FIG. 11 is a partial schematic side view of the distal member shown in FIG. 10, illustrating the distal expandable member in an expanded state.
Figure 12:
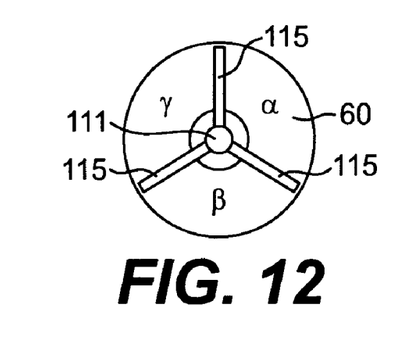
FIG. 12 is a schematic cross-sectional view of the distal member shown in FIG. 11, illustrating the distal member placed in a circular lumen for measurement of the lumen dimension, according to an exemplary embodiment of the invention.

The distal member 110 may include a main body 118 and one or more radially extendable arms 115. The arms 115 may be configured to bend radially outwardly to measure the inside diameter of a lumen. For example, each arm 115 may include three bending portions: distal bending portion 112, middle bending portion 113, and proximal bending portion 114, as shown in FIGS. 10 and 11. In various exemplary embodiments, at least one of the bending portions 112, 113, 114 may be formed of thinned-out sections to act as living hinges configured to bend in a predetermined direction or configuration when an axial force is exerted thereto. Proximate the distal bending portion 112, the arms 115 may be pivotally coupled to, or integrally formed (e.g., as a living hinge) with, a distal end portion 111 of the device 110 and, proximate the proximal bending portion 114, the arms 115 may be coupled to a control member 135. To facilitate the connection and/or uniformly apply axial force to the arms 115, a suitable connecting member, such as, for example, a ring 139, for connecting between the control member 135 and each of the arms 115 may be provided. In an alternative embodiment, especially when a non-circular lumen is being measured, a separate control member 135 may be provide for each arm 115 to individually control the movement of each arm 115. In an alternative embodiment, at least one of the arms 115 may be decoupled from the connecting member 139. In another alternative embodiment, a measurement device may not include a control member, but instead the arms 115 may extend to a proximal handle for their control.

In operation, when the control member 135 is moved distally to apply an axial force to the arms 115, the arms 115 may bend at the three bending portions to expand radially outwardly until the widest portion of the arm 115, preferably the middle bending portion 113, contacts the inner surface of a lumen being measured, as shown in FIG. 11. As described above, the measured diameter h of the distal member 110 may represent the diameter of the lumen being measured, and the measured value may be displayed on a suitable indicating member, such as, for example, the various embodiments described with reference to FIGS. 1-8.

Figure 13:
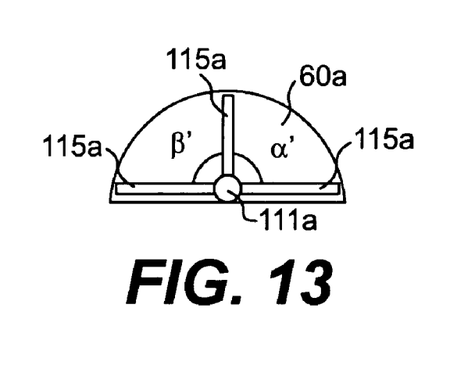
FIG. 13 is a schematic cross-sectional view of the distal member shown in FIG. 11, illustrating the distal member placed in a semi-circular lumen for measurement, according to another exemplary embodiment of the invention.
Figure 14:
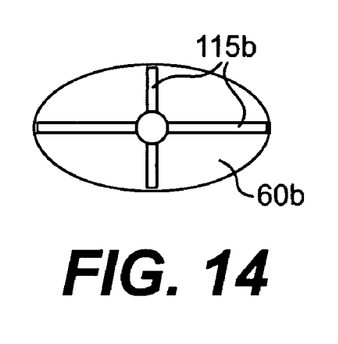
FIGS. 14-16 are schematic cross-sectional views of the distal member shown in FIG. 11, illustrating various exemplary embodiments of the distal member for measurement of various exemplary lumen shapes.
Figure 15:
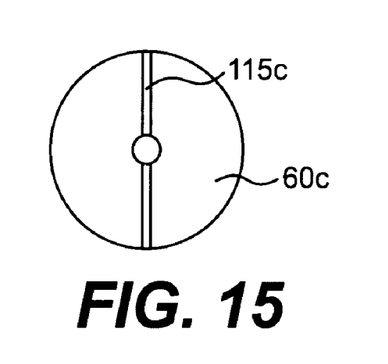
Figure 16:
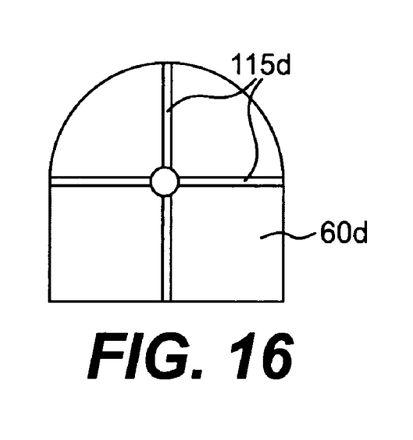

According to another exemplary embodiment of the invention, the radial spacing of the arms 115 may be symmetric or asymmetric, depending on, for example, the shape of the lumen being measured, as shown in FIGS. 12-16. For example, symmetric spacing of the arms 115, may be suitable for measuring a circular lumen 60 (e.g., α≈β≈γ), while asymmetric spacing of the arms 115, as shown in FIG. 13, may permit measurement of a non-circular lumen (e.g., semicircular, elliptical, D-shaped, or collapsed shape). In particular, for measurement of a particular non-circular lumen, such as the lumen 60a shown in FIG. 13, the arms 115a may be asymmetrically spaced (e.g., α'≠β') at various radial locations to measure the distance between the inner surface of the lumen and the center of the distal member 110. Of course, symmetrically spaced arms 115 may also be used for a non-circular lumen, as shown in FIGS. 14 and 16. While the embodiments shown in FIGS. 12 and 13 have a total of three arms 115, embodiments of the invention may include more or less than three arms 115b, 115c, 115d, as shown in FIGS. 14-16.

Figure 17A:
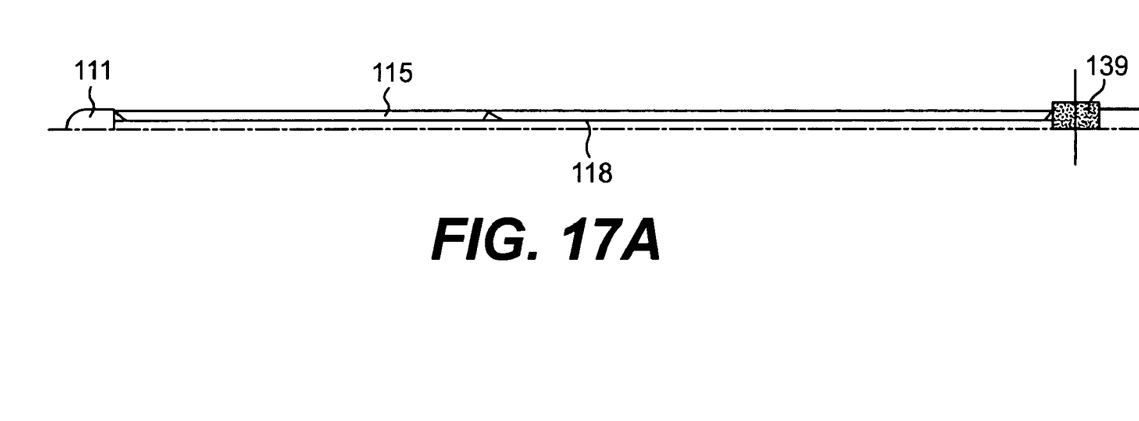
FIGS. 17A and 17B are partial schematic side views of a distal member of a lumen measurement device, according to another exemplary embodiment of the invention, illustrating an expansion of the distal member from a contracted state (FIG. 17A) to an expanded state (FIG. 17B)
Figure 17B:
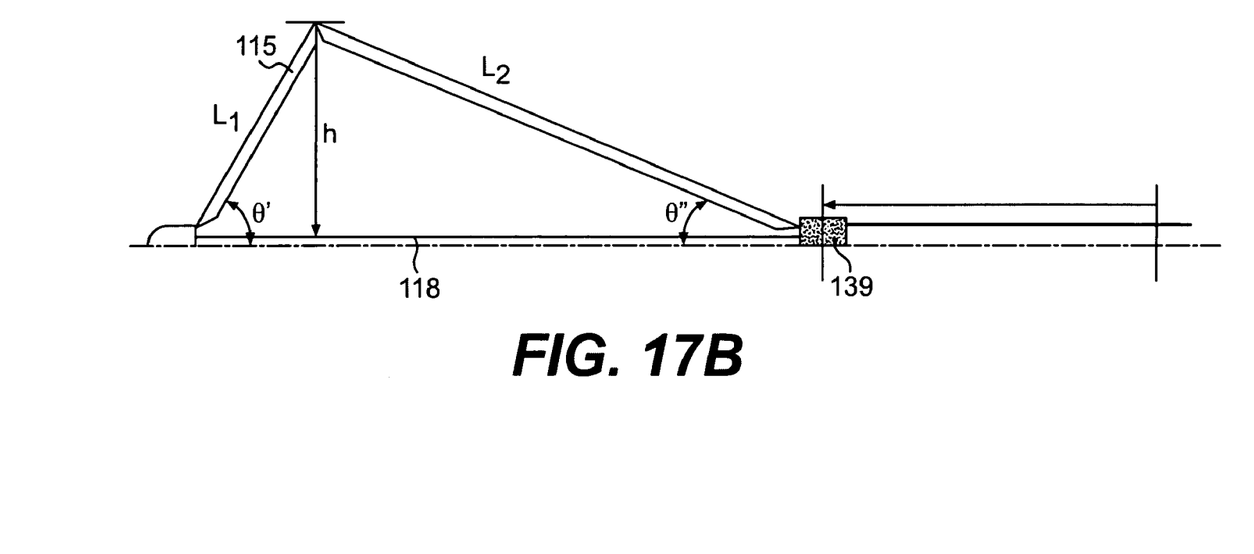

According to still another embodiment of the invention, the radius or diameter of a lumen may be determined by measuring the crank angle of the side arm 115 and/or the position of the connecting member 139. For example, as shown in FIGS. 17A and 17B, the radial extension or height h of the arm 115 may be determined from a previously determined correlative relationship between the axial position of the connecting member 139 and the height h. Alternatively or additionally, the height h may be determined by using one of the two crank angles θ', θ" formed between the main body 118 and the arm 115, as shown in FIG. 17B. For example, since the height h is proportional to the crank angles θ', θ" (e.g., h=$L_1$ sin θ'=$L_2$ sin θ") and the crank angles θ', θ" are proportional to the position of the connecting member 39, the height h of the arm 115 may be readily determined by measuring at least one of the crank angles and the connecting member position. The correlated relationship may be tabularized for quick referencing or stored as a database readily accessible by a suitable computer program used by a physician. In an alternative or additional embodiment, the correlated relationship may be programmed or built into the measurement device.

Figure 18:
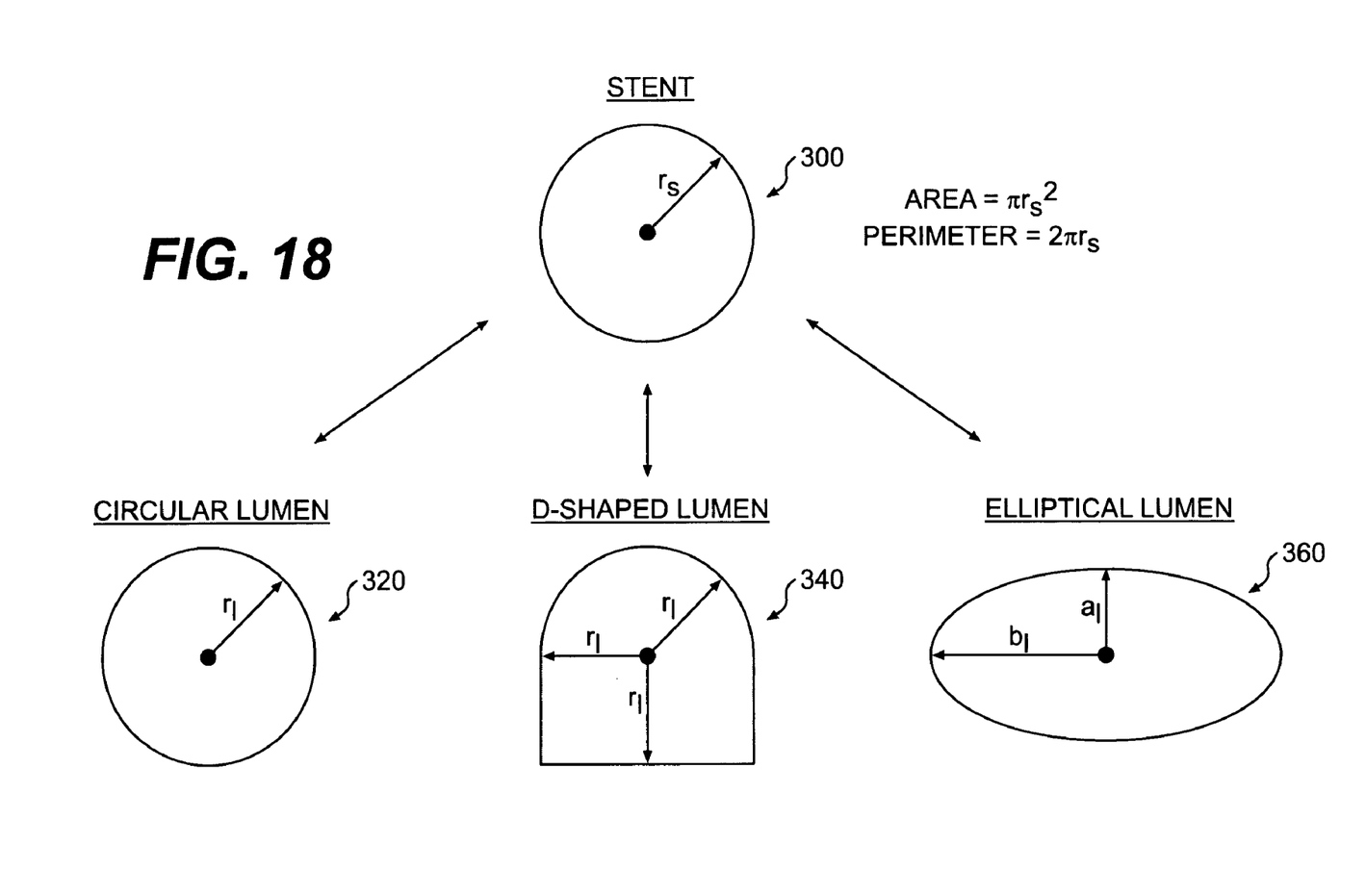
FIG. 18 is a schematic illustration for an exemplary method of converting a measured value of a lumen to a normalized value of a circular lumen.

According to another aspect of the invention, once a lumen is properly measured, the measured value of the lumen may be converted into an actionable value, such as, for example, a normalized area or diameter of the lumen, so that a suitable stent for use in the lumen may be selected. With reference to FIG. 18, various exemplary methods of converting measured radius or diameter of a circular or non-circular lumen 320, 340, 360 to a normalized radius or diameter of a circular stent 300 are discussed in detail.

For a substantially circular lumen 320, the measured radius $r_l$ of the lumen 320 may simply be assumed to be equal to the radius $r_s$ of a circular stent 300 (i.e., $r_l$=$r_s$). For a non-circular lumen, such as, for example, D-shaped lumen 340 or elliptical lumen 360 shown in FIG. 18, the perimeter or cross-sectional area of the lumen 340, 360 may be equated to the perimeter or cross-sectional area of a circular stent 300 to determine the diameter of the circular stent 300 that will be deployed in that lumen 340, 360.

For example, the perimeter $P_l$ of the lumen 340 may be approximated by using simple geometric formulae, which yields $$P_l = \left(\frac{1}{2} \cdot 2\pi \cdot r_l\right) + 4r_l = r_l(\pi + 4)$$

Since the perimeter $P_s$ of a circular stent is $P_s$=$2\pi \cdot r_s$, equating those two perimeters $P_l$ and $P_s$ yields $$r_l(\pi + 4) = 2\pi \cdot r_s \rightarrow \frac{r_l}{2} \cdot \left(1 + \frac{4}{\pi}\right) = r_s \rightarrow D_s = 2.2732 \cdot r_l,$$

where $D_s$ equals the diameter of the stent.

Similarly, for an elliptical lumen 360, the perimeter (i.e., circumference) $P_l$ of the lumen 360 may be approximated as $$P_l = 2\pi\sqrt{\frac{1}{2}(a_l^2 + b_l^2)},$$

which may be equated to the perimeter $P_s$ of a circular stent $P_s$, to yield $$r_s = \sqrt{\frac{1}{2}(a_l^2 + b_l^2)}.$$

The equation may be further simplified if one of the axis $a_l$, $b_l$ can be expressed as a function of the other axis $a_l$, $b_l$, to yield $$r_s = \sqrt{\frac{1}{2}(a_l^2 + [f(a_l)]^2)}.$$

For a special ellipse where $b_l$ is equal to ½ or ⅓ of $a_l$, the diameter $D_s$ of the stent 300 may be approximated as $$D_s = 2r_s = 2 \cdot \frac{\sqrt{10}}{4} \cdot a_l = 1.581 \cdot a_l \text{ and } D_s = 2r_s = 2 \cdot \frac{\sqrt{5}}{3} \cdot a_l = 1.491 \cdot a_l,$$

respectively.

Therefore, once appropriate values of a lumen are measured, the dimension (e.g., diameter, circumference, or cross-section area) of a stent, suitable for use in the lumen, may be accurately determined. Such an accurate assessment of the lumen dimension may permit a physician to confidently select a suitable stent and thereby effectively reduce problems of under/over-deployment or migration of a stent.

The operation of the lumen measurement device 1, according to an embodiment of the invention, will be described in detail with reference to FIGS. 19 and 20. While operational aspects of the invention will be described with an exemplary embodiment shown in FIGS. 1 and 2, the invention may be used with any other exemplary embodiments, without departing from the scope of the invention. In another exemplary embodiment, instead of measuring a lumen size, the invention may be applied to measure an axial extension or position of an extending member, such as needles, snares, or biopsy forceps, extending from a particular reference point of a medical device.

Figure 19:
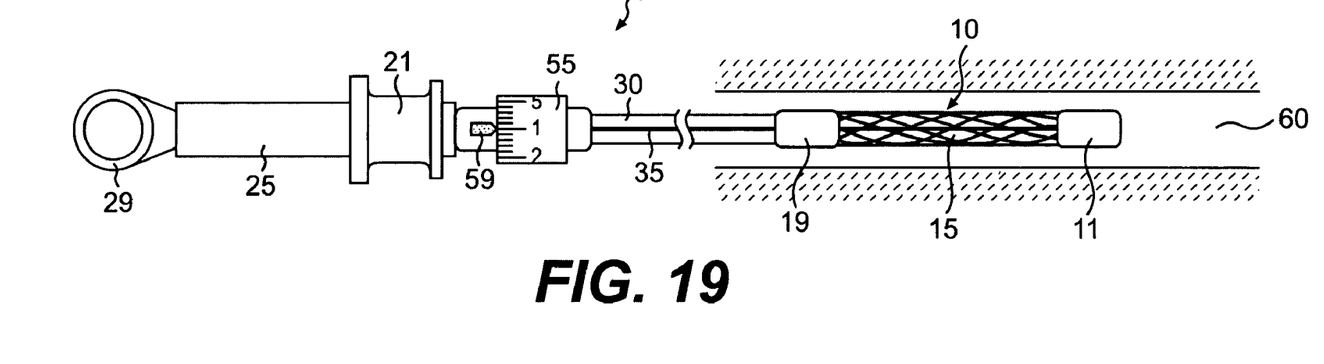
FIGS. 19-20 are schematic cross-sectional views of the lumen measurement device shown in FIG. 1, illustrating an exemplary method of measuring a lumen size, according to an embodiment of the invention.
Figure 20:
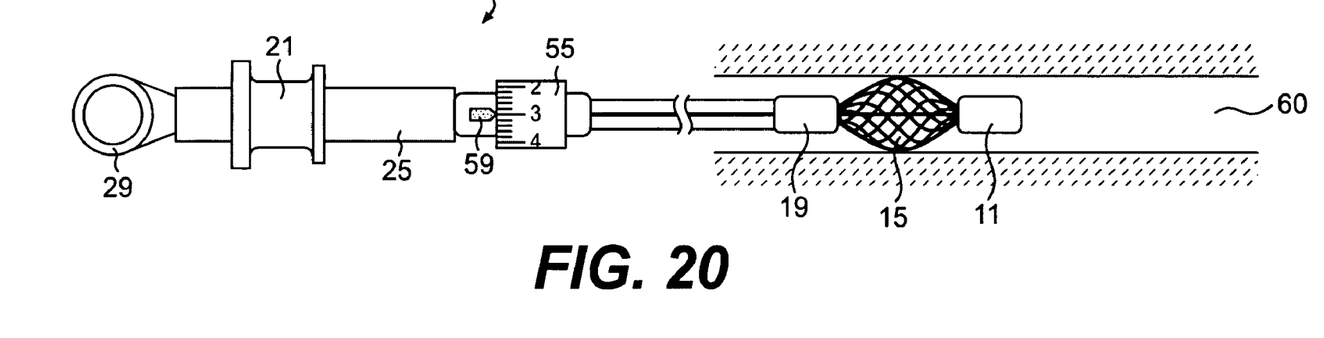

FIG. 19 illustrates a lumen measurement device 1 with its expandable distal member 10 in a contracted state. To attain this position, the spool 21 may be moved distally relative to the main body 25 to extend the control member 35 distally, causing the expandable member 15 to contract. This contracted state of the expandable distal member 10 may be the preferred position while inserting the device 1 into a body lumen 60. In this contracted state, the diameter of the expandable member 15 may be displayed on the indicating member 55. In the exemplary embodiment shown in FIG. 19, the initial diameter of the expandable member is 1 unit. With the expandable member 15 in the contracted state, the device 1 may be inserted into an endoscope lumen to position the distal member 10 near the measurement site in the lumen 60, as shown in FIG. 19. A suitable imaging device, such as, for example, an endoscope, colonoscope, or sigmoidoscope, may be used to aid in positioning the distal member 10 of the device 1.

Once the distal member 10 of the device 1 is properly positioned, the spool 21 may be moved proximally relative to the main body 25 to pull the control member 35 proximally, causing the expandable member 15 to expand, as shown in FIG. 15, until the widest portion of the expandable member 15 is brought into contact with an inner surface of the lumen 60. The diameter of the expandable member 15 may represent the actual diameter of the lumen 60 and may be displayed on the indicating member 55. In the embodiment shown in FIG. 20, the lumen diameter is 3 units.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device configured to be inserted into a body lumen and used to measure a size of the body lumen, comprising:
   a proximal handle assembly;
   a distal member including a proximal end member distal the proximal handle assembly, a distal end member distal the proximal end member, and a radially expandable member connected to the proximal end member and the distal end member and configured to expand from a contracted state to an expanded state within the body lumen to measure the size of the body lumen;
   a control member fixedly connected to the proximal handle assembly and directly and fixedly connected to the distal end member of the distal member such that the control member and the distal end member are immovable relative to each other, actuation of the proximal handle assembly causing the expandable member to expand; and
   a measurement indication member for displaying a value indicative of a size of the expandable member.

2. The device of claim 1, wherein the indication member is located proximate the distal member.

3. The device of claim 1, wherein the indication member is located proximate the proximal handle assembly.

4. The device of claim 3, wherein the indication member is integrally formed with the handle assembly.

5. The device of claim 1, wherein the indication member includes a rotatable member configured to rotate in relation to expansion and contraction of the expandable member; the rotatable member including a plurality of measurement marks for displaying the size of the expandable member.

6. The device of claim 5, wherein the rotatable member is configured to interact with the control member to rotate in relation to expansion and contraction of the expandable member.

7. The device of claim 6, wherein the rotatable member and the control member are configured to translate axial movement of the control member into rotational movement of the rotatable member.

8. The device of claim 6, wherein the rotatable member is a cylindrical member having at least one projection protruding from an inner surface of the cylindrical member.

9. The device of claim 8, wherein the control member includes a spiral configuration such that the cylindrical member rotates as the control member moves axially.

10. The device of claim 1, wherein the value displayed on the measurement indication member includes at least one of diameter, radius, circumference, and cross-sectional area of the expandable member.

11. The device of claim 1, wherein the value displayed on the measurement indication member includes a type of other device suitable for use in the lumen.

12. The device of claim 1, wherein the expandable member includes a proximal end and a distal end and is configured to radially outwardly expand upon a relative movement of the proximal and distal ends towards each other.

13. The device of claim 12, wherein the expandable member includes a plurality of wires.

14. The device of claim 13, wherein the plurality of wires are intermeshed to form a radially expandable sleeve.

15. The device of claim 12, wherein the expandable member includes a bending portion to allow the expandable member to bend in a predetermined direction upon the relative movement.

16. The device of claim 12, wherein at least one of the distal and proximal ends is coupled to the control member to cause the relative movement between the distal and proximal ends.

17. The device of claim 12, wherein:
the control member includes a plurality of control members and the expandable member includes a plurality of expandable members; and
each of the plurality of control members is connected to a corresponding one of the plurality of expandable members.

18. The device of claim 12, wherein the expandable member comprises a plurality of expandable members symmetrically arranged in a radial direction.

19. The device of claim 12, wherein the expandable member comprises a plurality of expandable members asymmetrically arranged in a radial direction.

20. The device of claim 1, wherein the distal member is an integral, single-piece member.

21. The device of claim 1, wherein the expandable member includes at least two expandable members, one of the at least two expandable members being configured to be decoupled from the other of the at least two expandable members.

22. The device of claim 1, wherein the expandable member includes at least two expandable members, one of the at least two expandable members being configured to expand and/or contract relative to the other of the at least two expandable members.

23. The device of claim 1, wherein axial movement of the proximal handle assembly causes the radially expandable member to expand to the expanded state.

24. The device of claim 1, wherein the control member extends through the radially expandable member of the distal member.

25. The device of claim 1, wherein a distalmost end of the control member and the distal end member do not move relative to each other.

26. The device of claim 1, wherein the proximal end member is fixedly connected to a tubular member extending from the proximal handle assembly.

27. A measurement device configured to be inserted into a body lumen and used to measure a size of the body lumen, comprising:
a proximal handle assembly;
a distal member including a proximal end member distal the proximal handle assembly, a distal end member distal the proximal end member, and an axially extendable member connected to the proximal end member and the distal end member and configured to extend from a first position to a second position within the body lumen to measure the size of the body lumen;
a control member fixedly connected to the proximal handle assembly and directly and fixedly connected to the distal end member of the distal member such that the control member and the distal end member are immovable relative to each other, actuation of the proximal handle assembly causing the extendable member to extend; and
a measurement indication member for displaying a value indicative of at least one of an axial extension or a position of the extendable member.

28. The device of claim 27, wherein the indication member is located proximate the distal member.

29. The device of claim 27, wherein the indication member is located proximate the proximal handle assembly.

30. The device of claim 27, wherein the indication member includes a rotatable member configured to rotate in relation to extension and retraction of the extendable member; the rotatable member including a plurality of measurement marks for displaying the axial extension or the position of the extendable member.

31. The device of claim 30, wherein the rotatable member is configured to interact with the control member or the extendable member to rotate in relation to extension and retraction of the extendable member.

32. The device of claim 31, wherein the rotatable member is configured to translate axial movement of the control member or extendable member into rotational movement of the rotatable member.

33. The device of claim 30, wherein the rotatable member is a cylindrical member having at least one projection protruding from an inner surface of the cylindrical member.

34. The device of claim 33, wherein the control member includes a spiral configuration such that the cylindrical member rotates as the control member moves axially.

35. The device of claim 27, wherein axial movement of the proximal handle assembly causes the axially extendable member to extend.

36. The device of claim 27, wherein the control member extends through the axially extendable member of the distal member.

37. The device of claim 27, wherein a distalmost end of the control member and the distal end member do not move relative to each other.

* * * * *